United States Patent
Sarangapani

(10) Patent No.: US 7,381,751 B2
(45) Date of Patent: *Jun. 3, 2008

(54) ANTIMICROBIAL COMPOSITION FOR MEDICAL ARTICLES

(76) Inventor: Shantha Sarangapani, 17 Rose Marie La., Walpole, MA (US) 02081

( * ) Notice: Subject to any disclaimer, the term of this patent is extended or adjusted under 35 U.S.C. 154(b) by 338 days.

This patent is subject to a terminal disclaimer.

(21) Appl. No.: 10/925,631

(22) Filed: Aug. 25, 2004

(65) Prior Publication Data

US 2005/0048124 A1  Mar. 3, 2005

Related U.S. Application Data

(60) Provisional application No. 60/497,967, filed on Aug. 26, 2003.

(51) Int. Cl.
  A61K 47/30   (2006.01)
  A61K 33/42   (2006.01)
  A61K 33/38   (2006.01)
  A61K 33/34   (2006.01)
  A61K 33/00   (2006.01)
  A61K 31/28   (2006.01)
  A01N 59/26   (2006.01)
  A01N 59/16   (2006.01)
  A01N 59/20   (2006.01)
  A01N 59/02   (2006.01)

(52) U.S. Cl. .............. 514/772.3; 424/604; 424/618; 424/630; 424/704; 514/495; 514/836

(58) Field of Classification Search ........... 424/704, 424/604, 618, 630, 544; 604/544; 514/495, 514/836, 772.3

See application file for complete search history.

(56) References Cited

U.S. PATENT DOCUMENTS

| 4,603,152 A | * | 7/1986 | Laurin et al. ............... 604/265 |
| 5,877,243 A | * | 3/1999 | Sarangapani ................ 524/139 |
| 5,894,042 A | * | 4/1999 | Ferralli ..................... 428/36.91 |
| 6,974,588 B1 | * | 12/2005 | Miranda et al. ............ 424/448 |
| 2005/0004525 A1 | * | 1/2005 | Sarangapani et al. ....... 604/174 |

* cited by examiner

Primary Examiner—Johann R. Richter
Assistant Examiner—Ernst Arnold
(74) Attorney, Agent, or Firm—Richard D. Fuerle

(57) ABSTRACT

An antimicrobial composition is formed from about 5 to about 25 wt % of an antimicrobial formulation and about 75 to about 95 wt % of a silicone resin. The antimicrobial formulation is formed from about 60 to about 95 wt % of an antimicrobial material, about 1 to about 30 wt % calcium chelator, about 0.001 to about 0.25 wt % pigment, and about 0.5 to about 3.5 wt % lubricant. The silicone resin may be a dispersion of about 40 to about 60 w/v % of an RTV silicone resin in a solvent, a liquid silicone resin, or a solid silicone resin. An antimicrobial coating may be formed on the surface of an article by applying an antimicrobial composition to the article and permitting the solvent to evaporate. It may also be formed by making a mixture of about 5 to about 12 wt % of an antimicrobial formulation and about 88 to about 95 wt % of a liquid or solid silicone resin and molding, overmolding, or extruding the article from the compounded mixture.

22 Claims, No Drawings

ANTIMICROBIAL COMPOSITION FOR MEDICAL ARTICLES

CROSS REFERENCE TO RELATED APPLICATION

This application claims priority from provisional application No. 60/497,967, filed Aug. 26, 2003.

BACKGROUND OF THE INVENTION

This invention relates to an antimicrobial formulation that can be used with silicone and silicon resins to coat products that have silicone surfaces or are 100% silicone, such as medical devices. It can also be directly incorporated into medical devices and products used for non-medical applications. In particular, it relates to antimicrobial formulations that can be blended with a room temperature vulcanizing (RTV) silicone resin (for coating applications) or compounded with liquid silicone rubber (LSR) materials (for extruding or overmolding applications). The antimicrobial formulations comprise an antimicrobial material, a calcium chelator, a pigment, and a lubricant.

Silicone is a soft, highly flexible and non-toxic material extensively used for several types of medical devices, including catheters, stents, Foley catheters used for incontinence, other urological catheters, gastrostomy tubes, feeding tubes, and certain consumer products. Silicone, like other materials, is susceptible to bacterial adherence, which leads to the formation of biofilms and the encrustation of calcium deposits when used in contact with body fluids such as urine, blood, bile, etc. The presence of bacteria on medical articles can result in infections and the spreading of diseases.

SUMMARY OF THE INVENTION

Silicone surfaces are difficult to coat with other polymers, but in this invention this problem has been overcome. A coating on the surface of an article is achieved either by coating the article with a composition containing a room temperature vulcanizing (RTV) silicone resin or by compounding an antimicrobial formulation with a liquid or solid silicone resin, which is molded, overmolded, or extruded into the article. The coating becomes integrated with the surface of the article and does not delaminate, swell, or separate. Due to the slow release of the antimicrobial material, such surfaces show a consistent and continuous antimicrobial activity when challenged with microorganisms.

The principal object of the present invention is to produce an antimicrobial composition that is useful for coating medical articles, or can be incorporated into medical articles, to prevent the formation of biofilms and encrusting deposits thereon.

Another object of the present invention is to provide a coatable composition that includes an RTV silicone resin dissolved in a solvent.

It is yet another object of this invention to provide coatable compositions for urinary catheters, urological devices, feed tubes, gastric buttons, and other types of catheters that are made of silicone, and enhance the lubricity of the surface of a medical article by releasing a lubricious, non-toxic compound from a coating of the composition.

Yet another object of this invention is to provide antimicrobial silicone coatings for silica particles, surface modified silica based ceramics, textile finishes, filament wound water filters, cartridges, storage tanks, sealing caps, glove linings, gloves, and fabric coatings such as water repellent finishes.

Another object of this invention is to provide a chemical formulation for direct blending with liquid silicone materials for direct extrusion or overmolding onto an article.

DESCRIPTION OF THE PREFERRED EMBODIMENTS

The Antimicrobial Composition

The antimicrobial composition of this invention has two parts, an antimicrobial formula with four components and a silicone resin, which may be an RTV, a liquid silicone, or a solid silicone resin.

Part I (Antimicrobial Formulation)
(1) antimicrobial material;
(2) calcium chelator;
(3) pigment; and
(4) lubricant.
Part II (Silicone Resin)

The purpose of the antimicrobial material is to kill bacteria, yeasts, and molds. Examples of suitable antimicrobial materials include nanosize particles of metallic silver or an alloy of silver containing about 2.5 wt % copper (hereinafter referred to as "silver-copper"), salts such as silver citrate, silver acetate, silver benzoate, bismuth pyrithione, zinc pyrithione, zinc percarbonates, zinc perborates, bismuth salts, various food preservatives such as methyl, ethyl, propyl, butyl, and octyl benzoic acid esters (generally referred to as parabens), citric acid, and sodium percarbonate. The preferred antimicrobial materials are silver, partially water soluble compounds of silver, silver pyrithione, zinc pyrithione, bismuth pyrithione, parabenzoic acid esters, and mixtures thereof. Silver particles having a particle size of about 1 to about 100 nm are believed to slowly release silver ions, Ag+, which are antimicrobial. Silver and silver salts, such as silver citrate, are especially preferred, because they are very effective and safe bactericides due to their rapid release of silver ions. Butyl paraben and octyl paraben are the preferred antimicrobial materials for yeasts and molds due to their low solubility in water. About 65 to about 95 wt % of the antimicrobial formulation may be the antimicrobial material; less is ineffective. Preferably, about 40 to about 65 wt % of the antimicrobial material is used in the formulation of which about 15 to about 25 wt % is silver, silver-copper, a partially water soluble silver salt, or a mixture thereof and about 25 to about 40 wt % is parabenzoic acid esters. The antimicrobial material slowly leaches from the formulation, keeping the coated surface free of live bacteria, yeasts, and molds.

The calcium chelator prevents deposits of calcium and/or magnesium from forming, which may impede the flow of urine. Examples of suitable chelators include EDTA (acid form), citric acid, hydroxyethylidene phosphonic acid, polyvinylphosphoric acid, polyvinylsulfonate, acrylic acid, and aminophosphonic acid. The preferred chelators are citric acid and EDTA (acid form) because of their ability to solubilize silver and form complexes with calcium ions. About 1 to about 55 wt % (based on the weight of the antimicrobial formulation) may be chelator. More is undesirable because of its acidity and less is undesirable because the efficacy of the long term release may be reduced. Preferably, the chelator is about 20 to about 25 wt % citric acid and about 20 to about 25 wt % EDTA (acid form).

The purpose of the pigment is for coloring, as the silver imparts a dark grayish color. The addition of the pigment imparts a bluish gray shade. Copper phthalocyanine (pigment blue) is the preferred pigment because it is believed to also have a bacteriostatic effect and is used in surgical sutures. FDA approved coloring pigments commonly used by the medical industry may also be used. About 0.001 to about 0.25 wt % (based on the weight of the antimicrobial formulation) may be pigment. More is undesirable because of the high intensity in color and the blocking effect of the large pigment molecules, and less is undesirable because the benefit of the color is lost (i.e., the color is visually not pleasing). Preferably, about 0.1 to about 0.25 wt % of the pigment is used.

The purpose of the lubricant is to make the surface lubricious, which is advantageous because it helps to prevent bacteria from adhering to the filter. Examples of suitable lubricants include polyethylene oxide, polyacrylic acid, polyvinylpyrrolidone, polyvinyl alcohol, and derivatives thereof. The preferred lubricant is polyethylene oxide because it discourages cell adhesion and can be incorporated into the antimicrobial formulation. About 3 to about 5 wt % (based on silicone solids in the formulation) is lubricant. More is undesirable because of it may make processing more difficult and less is undesirable because the surface may not be sufficiently lubricious. Preferably, about 4 to about 5 wt % lubricant is used.

The silicone resin helps a coating of the formulation to adhere to various surfaces. The silicone resin used in the composition of this invention may be a liquid silicone resin or a solid silicone resin, but it is preferably an RTV silicone resin. RTV silicone resins are available in one part (RTV-1) and two-part (RTV-2) systems. One part systems consist of polydialkylsiloxane with terminal hydroxyl groups, which are reacted with organosilicon cross-linking agents. The reaction is performed in a moisture-free environment and results in the formation of a tetrafunctional structure. Curing takes place when the materials are exposed to moisture. Atmospheric moisture is sufficient to trigger the reaction. The thickness of the coating should be limited if only one side of the it is exposed to a source of moisture. Curing is relatively slow, as it relies on moisture migrating into the polymer. The examples that follow use the one part system.

Two part systems can be divided into two categories, condensation cross-linked materials and addition cross-linked polymers. Condensation systems involve the reaction of silanol-terminated polydimethylsiloxanes with organosilicon cross-linking agents such as $Si(RO)_4$. Storage life depends on the catalyst employed and ambient conditions. Addition-cured materials must be processed under clean conditions as curing can be affected by contaminants such as solvents and catalysts used in condensation RTVs. Addition-cured materials are suitable for use with polyurethane casting materials. Of the two types of RTV silicone resins, the one part systems are preferred because they are easier to process.

The term "RTV silicone resin" is intended to include any silicone resin that can be dispersed in a solvent that can leave behind a solid resin. The preferred RTV silicone is made by General Electric Corp. and is sold as "GE-118." It is believed to have a composition of 1 to 5 wt % di-t-butoxydiacetoxysilane, 1 to 5 wt % methyltriacetoxysilane, 1 to 5 wt % octamethylcyclotetrasiloxane, 60 to 80 wt % dimethyl polysiloxane silanol/st, 5 to 10 wt % silanol/stpd siloxane with methyl silsesquioxanes, and 10 to 30 wt % amorphous silica. Other RTV silicone resins or silicone dispersions are that may be used are commercially available and may be purchased from General Electric, Bayer, Dow, and other companies. The mixture of the RTV silicone and the solvent should contain about 40 to about 60 w/v % RTV silicone and the remainder solvent (i.e., about 40 to about 60 gm of RTV silicone is dispersed in 100 mL of solvent) as less RTV silicone results in a low viscosity dispersion, causing the antimicrobial composition to settle faster, and the higher amount of solvent may pose a risk of chemical attack on the coated article. More than about 60 wt/v % RTV silicone makes dip coating difficult due to the higher viscosity. The preferred amount of RTV silicone in the mixture is about 48 to about 52 w/v %. The preferred amount helps to maintain a uniform suspension of the antimicrobial composition due to its higher viscosity, which keeps the particles suspended.

Any non-toxic organic solvent that will evaporate from a coating in a few hours at about 60° C. may be used as the solvent. Examples include hexanes (a mixture of hexane isomers), methyl ethyl ketone, xylenes (a mixture of xylene isomers), and similar solvents. The preferred solvent is hexane because it is less toxic than some of the other solvents and can be evaporated in a few hours at a temperature below about 60° C. The addition of the RTV silicone resin to the solvent may be performed with stirring at a temperature of about 15 to about 18° C.

In addition to RTV silicone resins, liquid and solid silicone resins may also be used to make articles that have antimicrobial coatings on their surfaces by incorporating the antimicrobial formulation into a resin that can be extruded or molded into an article, as hereinafter described. Resins suitable for extruding or molding into articles include silicone resins are commercially available. Silicone resins are preferred because of the ability to blend the antimicrobial formulation with a gum-like silicone resin. However, higher cure temperatures are required for extrusion than for conventional silicone resins.

Liquid silicone is similar in properties to normal silicone but varies in its processing characteristics. It is purchased as a two part raw material with a viscosity similar to Vaseline. It is supplied deaerated, ready for use, often in premetered equipment. The two materials are pumped from a drum through a mixing head and injected into the cavities. Very low pressures are involved and the cure time is very fast (typically 20 to 45 seconds) at temperatures of about 200° C. and post-curing is usually not required. The resin cures after mixing the two separate portions, by processes such as hydrosilylation. A full range of hardnesses can be achieved as well as colour matching in a very clean process. The fast cycles and low material usage offers a significant cost advantages on long runs Solid silicone rubbers that may be used with the antimicrobial formulation are usually cured using peroxides such as benzoyl peroxide, 2,4-dichlorobenzoyl peroxide, t-butyl perbenzoate, and dicumyl peroxide. Alkyl hydroperoxides and dialkyl peroxides have also been used successfully with vinyl containing silicones. Hydrosilylation and hydrosilation are alternative curing methods for vinyl contiaining silicones and utilize hydrosilane materials and platinum-containing compounds for catalysts. Curing does not produce volatiles and heat cured conventional silicones with high tear strengths can be cured this way. Dow Chemical Corp. and General Electric Corp. are major commercial producers of such resins. These resins may be cured at temperatures close to about 150° C. for short time or at room temperature for a longer period. Solid silicone resins typically require a cure temperature of about 300 to about 400° C.

Optional components may also be included in the antimicrobial formulation. For example, it is preferable to include about 0.5 to about 4 wt % of nanosize (20 to 40 nm)

high surface area titanium dioxide as a support for loading of the antimicrobial formulation and also to lighten the color. Zinc pyrithione or bismuth pyrithione are optional antimicrobial materials that may be included at very small percentages such as about 0.1 to about 0.5 wt % (based on the silicone in the formulation).

A preferred antimicrobial formulation is about 10 to about 16 wt % silver citrate, about 5 to about 70 wt % nanosize (i.e., less than about 100 nanometers) silver powder, about 5 to about 15 wt % EDTA or a vinyl phosphonic acid or hydroxy ethyl phosphonic acid, about 20 to about 40 wt % butyl paraben, and about 10 to about 22 wt % citric acid.

The antimicrobial composition of this invention may be prepared by finely blending the above-described components; blending may be performed, for example, in an industrial blender.

Uniform Blends of the Antimicrobial Formulation with Silicones of Different Types:

If an RTV silicone resin is used, a dispersion of the RTV silicone resin is preferably blended in as a solvent based dispersion using a sonicator after stirring in the other components. An optional amount of isopropyl alcohol at a level of about 0.1 to about 0.2% increases the pot-life of the coating formulation; however, the curing is considerably delayed.

For overmolding, or injection molding, the liquid silicone part 1 and part 2 are mixed while metering in the antimicrobial formulation, using static mixers. Commercial liquid silicone injection molding apparatus may be used. For conventional solid silicone resins, the antimicrobial formulation and other components may be directly mixed and compounded using a compounder, followed by extrusion.

Coating Surfaces

The antimicrobial coating composition of this invention may be used to coat the surfaces of articles to retard the growth of microbes thereon. Examples of articles that may be coated include silica particles, surface modified silica based ceramics, textile finishes, filament wound water filters, cartridges, storage tanks, sealing caps, glove linings, gloves, and fabric coatings such as water repellent finishes. While any surface may be coated with the composition, the composition is preferably used to coat the surfaces of medical devices such as catheters, stents, Foley catheters, gastrostomy tubes, feeding tubes, silicone coated latex type surfaces. silicone valves, balloons, septa, etc., that are prone to infection, silicone parts used in various medical pumps, tubings and earplugs, and as a textile finish for linings for hospital beds, window shades, and curtains. These articles may be made of various materials including plastics, metals, glass, and ceramics. Preferably, they are made of a polymeric material (a plastic), such as silicone, silicone coated plastics, and polyurethanes. The preferred material is silicone because the coating adheres better to silicone.

To coat a surface with the antimicrobial material, the surface is cleaned, if necessary, which may be done using, for example, a water-based detergent then drying thoroughly, or with an organic solvent such as ethanol, then drying and wiping the surface with hexane. The composition may be applied to the surface by any suitable technique. The following are examples of coating techniques that may be used, depending on the substrates:

Dip/immersion coating
Dip molding
Kiss coating (lick roll)
Knife coating (over air, roll or rubber sleeve)
Rotogravure coating
Spray coating
Other methods such as bar coating or rotary screen printing The preferred methods are dip coating and dip molding using a mandrel in the same shape as the article.

The solution or dispersion may have to be applied several times to the surface in order to achieve the desired thickness for the coating. The thickness of the coating should be about 0.5 to about 2 mils as thinner coatings may be less effective and thicker coatings may not be necessary. A preferred thickness is about 1 to about 2 mils. After each layer of coating is applied, the surface is dried. This may be accomplished, for example, by air drying or by warming the surface in an oven. The composition is preferably dried at room temperature followed by drying at about 50 to about 60° C. for about 3 to about 4 hours. Articles with balloons made of silicone, such as Foley silicone catheters, may be easily coated with the composition of this invention and were found to pass both the ASTM and the European standard test for balloon expansion in Foley catheters and the burst strength tests.

To form an article by dip molding, a mandrel in the shape of the article is heated, dipped into a tank holding an antimicrobial composition, and removed from the tank. Liquid or RTV silicone resins may be used in the antimicrobial composition, which is dissolved or dispersed in a solvent. The viscosity of the solution depends on its solids content, which can be increased by adding more solids or decreased by adding more solvent until the desired viscosity is attained. After dipping, the thin coating of the composition that remains on the surface of the mandrel is allowed to cure and/or cure, then is stripped off as a finished product. Multiple dipping steps may be used to increase the thickness of the coating and curing time, temperature, and speed of immersion may be adjusted to control the properties of the resulting article. Gloves, balloons, and other articles may be made by this process.

(B) Incorporation of the Formulation

The antimicrobial formulation of this invention may also be incorporated into an article, so that it will gradually leach to the surface of the article and form a coating on the surface that retards the growth of microbes thereon. When the formulation in this manner, a liquid or solid silicone resin is used instead of a RTV silicone resin and it is not necessary to form a dispersion of the silicone resin. Materials in which the formulation may be incorporated include silicone resins, liquid silicone, polyurethanes, polyvinyl chloride (PVC), and silicone-polyurethane blends. The preferred material is liquid silicone because of its ability to form conformal molded shapes and also conformal overmolded parts. This also avoids the need to use a solvent.

To incorporate the formulation into a material, the formulation is mixed with the material to produce a homogeneous mixture. The mixture may contain about 5 to about 12 wt % of the formulation; less formulation may not be sufficiently effective in retarding the growth of microbes and more formulation may adversely affect the properties of the material. Preferably, the formulation is about 5 to about 10 wt % of the mixture.

The mixture is then formed into a desired shape and is hardened. The article may be shaped by molding, overmolding, extrusion, or another process. Depending upon the resin used, hardening may occur as a result of exposure of the material to air, heat, moisture, or as the result of a chemical reaction that began when the resin was prepared.

The methods result in the formation of an excellent product that facilitates the slow release of antimicrobials to the surface. The silicone resin encapsulates the antimicrobial materials and releases them at a controlled rate. On exposure to aqueous fluids, such as various body fluids, the water soluble components of the antimicrobial formulation migrate to the surface, where an equilibrium between the silver, citric acid, and EDTA is established. This is important because silver ions are rendered insoluble due to the formation of silver chloride or phosphates in the presence of body fluids. The presence of EDTA, which complexes silver ions, forming soluble complexed species of silver, allows a continuous migration of these soluble species to the surface despite the presence of chloride ions. The presence of the other components of the formulation, such as parabens (para benzoic acid esters) and copper phthalocyanine, help to keep the surface of the coated article antimicrobial. The lubricant imparts a slippery feel when wetted with water; this property allows the insertion of the catheter without causing trauma to the patient. More importantly, the lubricant elutes continuously from the coating, keeping the surface hydrophilic and lubricious, thereby discouraging the adherence of bacteria.

Incorporation of the antimicrobial formulation into an article is preferred to coating a surface with the composition as it is a less time-consuming procedure.

The following examples further illustrate this invention.

EXAMPLE 1

The following chemicals were blended:

(1) 3.0 g (16.12 wt %) silver citrate (Sigma-Aldrich Chemical, USA)

(2) 1.5 g (8.0 wt %) silver-copper alloy nanopowder (Nanopowder Ind, Israel)

(3) 3.0 g (16.12 wt %) citric acid (Sigma-Aldrich)

(4) 8.9 g (43.0 wt %) butyl paraben (Spectrum Chemicals, USA)

(5) 3.0 g (16.12 wt %) ethylene diamine tertaacetic acid, acid form (Sigma-Aldrich)

(6) 0.1 g (0.05 wt %) copper phthalocyanine (Spectrum Chemical)

Ten grams of this blend was added to another 0.25 gm of copper phthalocyanine and 150 mL of dry n-hexane. To that mixture was added 75 gm of "RTV 118" (McMaster Co, N.J., USA). To this was slowly added 5 gms dry pulverized polyethylene oxide (MW 4,000,000). Using a homogenizer, the contents were mixed well and transferred to a dipping tank, forming a dispersion containing about 1 to 15 wt % antimicrobial formulation.

The silicone surfaces of 3 silicone Foley catheters were cleaned by wiping with n-hexane. The catheters were dip-coated once by immersing them for a minute or two in the solution at room temperature. After a few seconds, the catheters were dip coated a second time. The coated catheters were allowed to air dry for a few minutes (1 to 3 minutes) and were then dried in a convection oven at 75 to 85° C. for 30 minutes. The catheters were removed and kept in a dark area. (The coated articles are preferably stored in light proof packages because the coating tends to darken on direct exposure to light.) When challenged with organisms such as clinical strains of species of *E. coli, Enterococcus*, and *Candida*, the coated catheters resisted the formation of biofilms significantly better than the uncoated catheters.

EXAMPLE 2

Composition A

The following formulation was prepared without titanium dioxide:

16.1 wt % silver citrate
8.0 wt % silver-copper
16.0 wt % citric acid
43 wt % butyl paraben
16 wt % EDTA, acid form
1 to 3 wt % copper phthalocyanine The ingredients were weighed and ground to a fine powder in an industrial blender. Prior to coating, 5 wt % polyethylene oxide (based on the weight of the RTV silicone resin to be added), was added to the powder and ground well. The composition was kept dry, in closed containers or in a low temperature oven.

Composition B

A second formulation was prepared with titanium dioxide.

10.5 wt % silver citrate
5.3 wt % silver-copper
21.0 wt % citric acid
42 wt % butyl paraben
10.5 wt % EDTA, acid form
4.2% copper phthalocyanine
6.3 wt % titanium dioxide Prior to coating, 5 wt % polyethylene oxide (based on the RTV silicone resin weight to be added), was added separately. Alternatively, the polyethylene oxide can be blended with the compositions under very dry conditions, preferably with the powder, prior to preparing the coating formula.

EXAMPLE 3

Using a 200 mesh screen, 4 gms of the powder compositions 2A and 2B were sieved and dried in an oven at about 50° C. for 30 minutes. Polyethylene oxide powder was also sieved using a 325 mesh screen and dried at about 50° C. for 30 minutes to an hour. The polyethylene oxide and the powder composition were mixed together under dry conditions. Then 6 gm of "GE 118" RTV silicone resin was diluted with 60 gm of hexane that had been dried using molecular sieves. The mixture of the polyethylene oxide and the powder composition were slowly mixed and the new mixture was sonicated at level 3 for 8 minutes. Then 26 gm of "GE 118" RTV silicone resin was stirred in at room temperature.

Articles were dipped into the solution 1 to 3 times, each time drying the coating for at least 15 minutes at room temperature. The coatings were air-dried under ambient humid conditions overnight followed by further drying at 60° C. for 1 to 2 hrs.

In this example, duplicate samples of catheters coated with five different compositions and one uncoated control catheter were cut into 2-cm length samples and placed in separate sterile tubes. 50 µl of a vancomycin-resistant *enterococcus fecalis* (VRE) cell solution (clinical isolate from UTI), 0.5 McFarland, was inoculated into a 12.5 ml "artificial urine" solution prepared by the procedure described in "An Improved Model for Bacterial Encrustation Studies," by S. Sarangapani, D. Gage, and K. Cavedon, *J. Biomed. Mater. Sci.*, 29, 1185 (1995), herein incorporated by reference. The inoculum solution was plated to confirm that the concentration of VRE cells was $1\times10^5$ on Day 0. 1 mL of the synthetic urine solution and 1 mL of the inoculum culture were added to each tube containing the catheter samples, and the tubes were incubated at 36° C., rotating at 20 rpm (Day 0).

Upon completion of various incubation times (days 1, 2, 4, and 7), the following assays were performed separately on the duplicate samples for each day of incubation:

1 mL of the synthetic urine solution and 1 mL of the inoculum culture were added to each tube containing the catheter samples, and the tubes were incubated at 36° C., rotating at 20 rpm On Day 0, there was planctonic growth on the contacting solution (CS). The attached viable cells (biofilm) on the catheter pieces (S) were counted.

On Day 4, a set of all the catheter samples was transferred to new test tubes and a fresh solution of artificial urine was added.

On Day 7, these samples were assayed for planctonic growth of the contacting solution (CS) and for attached viable cells (biofilm) (S). They are designated as DAY 7+.

The protocols for these assays are listed in Appendix A.
The results of this experiment are summarized in Table 1.

TABLE 1

VRE experiment (CFU/ml)

ENTEROCOCCUS TEST

| CATHETER TYPE | SAMPLE | DAY 1 | | DAY 2 | | DAY 4 | | DAY 7 | | DAY 7+ | |
|---|---|---|---|---|---|---|---|---|---|---|---|
| | | S | CS | S | CS | S | CS | S | CS | S | CS |
| $C_4$ | A | $<10^3$ | $<10^3$ | $<10^3$ | $<10^3$ | $<10^3$ | $<10^3$ | $<10^3$ | $<10^3$ | $<10^3$ | $<10^3$ |
| | B | $<10^3$ | $<10^3$ | $<10^3$ | $<10^3$ | $<10^3$ | $<10^3$ | $<10^3$ | $<10^3$ | $<10^3$ | $<10^3$ |
| | $\epsilon$ | $<10^3$ | $<10^3$ | $<10^3$ | $<10^3$ | $<10^3$ | $<10^3$ | $<10^3$ | $<10^3$ | $<10^3$ | $<10^3$ |
| D | A | $7 \times 10^5$ | $8 \times 10^6$ | $1.6 \times 10^6$ | $3 \times 10^7$ | $10^5$ | $2 \times 10^7$ | $10^4$ | $2 \times 10^7$ | $6 \times 10^5$ | $4 \times 10^7$ |
| (uncoated | B | $8 \times 10^5$ | $5 \times 10^6$ | $5 \times 10^5$ | $2 \times 10^7$ | $6 \times 10^5$ | $4 \times 10^7$ | $3 \times 10^4$ | $10^7$ | $4 \times 10^4$ | $10^7$ |
| control) | $\epsilon$ | $7.5 \times 10^5$ | $6.5 \times 10^6$ | $1.05 \times 10^6$ | $2.5 \times 10^7$ | $3.5 \times 10^5$ | $3 \times 10^7$ | $2 \times 10^4$ | $1.5 \times 10^7$ | $3.3 \times 10^5$ | $2.5 \times 10^7$ |
| BARDEX | A | $5 \times 10^5$ | $8 \times 10^8$ | $2 \times 10^4$ | $3 \times 10^8$ | $9 \times 10^4$ | $2 \times 10^7$ | $2 \times 10^4$ | $2 \times 10^7$ | $10^4$ | $2 \times 10^7$ |
| | B | $6 \times 10^5$ | $7 \times 10^8$ | $3 \times 10^4$ | $3 \times 10^8$ | $5 \times 10^4$ | $2 \times 10^7$ | $2 \times 10^5$ | $3 \times 10^6$ | $4 \times 10^4$ | $3 \times 10^7$ |
| | $\epsilon$ | $5.5 \times 10^5$ | $7.5 \times 10^8$ | $2.5 \times 10^4$ | $3 \times 10^8$ | $7 \times 10^4$ | $2 \times 10^7$ | $1.1 \times 10^5$ | $1.15 \times 10^7$ | $2.5 \times 10^4$ | $2.5 \times 10^7$ |

Note:
($\epsilon$) = average of the duplicate samples.

Tubes coated according to this invention showed silver leaching of 1.5 to 2 ppm in minimum essential medium extractions when extracted under UXP (United States Pharmacopia) recommended procedure conditions. However, when extracted with PBS (phosphate buffered saline), the silver in the USP extracts was less than 0.2 ppm.

Appendix A—Protocol of Assays

Planctonic growth assay of contacting solution (CS):
1. Vortex sample in its contacting solution for 10 seconds, then remove sample to tube with 2 mL of sterile PBS.
2. Plate 1 ml of at least two dilutions of the contacting solution onto tryptic soy agar+5% defibrinated sheep blood (TSA+5% DSB) agar plates.
3. Incubate plates at 37° C. for 24 to 48 hours. Determine CFU (colony forming units) by viable plate count method.

Biofilm Assay (S):
1. Remove planctonic cells from biofilm: Vortex sample in sterile PBS for 10 seconds, then transfer it to a second 2 mL PBS tube and vortex again.
2. Disaggregate bacteria by vortexing 10 seconds and sonicating at 35 KHz for 5 minutes on ice.
3. Plate 1 ml of at least two dilutions onto TSB+5% DSB agar plates.
4. Incubate plates at 37° C. for 24 to 48 hours. Determine CFU by viable plate count method.

EXAMPLE 4

Duplicate samples of two silicone catheters, one coated and one uncoated control, were cut into 2-cm length samples and each was placed in a separate sterile tube. Inoculum cultures of $1\times10^5$ E. coli cells/mL (clinical isolate from UTI) in synthetic urine were prepared. 1 mL of synthetic urine solution and 1 mL inoculum culture were added to each tube containing the catheter samples, and the tubes were incubated at 36° C., rotating at 20 rpm. (Day 0)

Upon completion of incubation time (Days 1, 4), the following assays were performed on separate duplicate samples for each day of incubation:
(1) planktonic growth of the contacting solution (CS); and
(2) counting of attached viable cells (biofilm) on the catheter pieces (S).

The protocols for these assays are listed in Appendix A. The dilutions tested were: 1:10, $10^2$, $10^3$, $10^4$.

The results of the preliminary experiment are summarized in Table 2.

TABLE 2

Preliminary experiment
Preliminary test E. coli (CFU/ml)

| CATHETER TYPE | TIME | DAY 1 S | DAY 1 CS | DAY 4 S | DAY 4 CS |
|---|---|---|---|---|---|
| Control (D) | A | $10^5$ | $2 \times 10^7$ | $10^5$ | $6 \times 10^8$ |
|  | B | $10^5$ | $10^7$ | $4 \times 10^5$ | $2 \times 10^8$ |
|  | Ave | $10^5$ | $1.5 \times 10^7$ | $2 \times 10^5$ | $4 \times 10^8$ |
| Coated (C-2) | A | $<10^3$ | $<10^3$ | $10^3$ | $10^3$ |
|  | B | $<10^3$ | $<10^3$ | $<10^3$ | $10^3$ |
|  | Ave | $<10^3$ | $<10^3$ | $10^3$ | $10^3$ |

Note:
Ave is the average of the duplicate samples.

On Day 1 of this experiment, the S and CS solutions were plated in parallel onto MacConkey plates. The results were comparable and therefore it was decided to continue with the more selective MacConkey plates for the evaluation of the different catheters.

Evaluation of Different Catheters with E. Coli

Duplicate samples of 5 different coated catheters, and one uncoated control catheter, were cut into 2-cm length samples and each was placed in a separate sterile tube. An inoculum culture of $1\times10^5$ E. coli cells/mL (clinical isolate from UTI) in synthetic urine was prepared. 1 mL of the synthetic urine solution and 1 mL of the inoculum culture were added to each tube containing the catheter samples and the tubes were incubated at 36° C., rotating at 20 rpm (Day 0).

Upon completion of the incubation times (Days 1, 2, 4, and 7), the following assays were performed on separate duplicate samples for each day of incubation:
(a) planktonic growth of the contacting solution (CS); and
(b) counting of attached viable cells (biofilm) on the catheter pieces (S).

On Day 4, only the contacting solution was assayed. The catheter samples were not sonicated, but rather were transferred to new test tubes with a fresh challenge of $1\times10^5$ E. coli cells. After an additional 3 days (which corresponded to Day 7 of the overall experiment), these samples were assayed for planctonic growth of the contacting solution (CS) and for attached viable cells (biofilm) (S). They are designated as DAY 7+. The protocols for these assays are listed in Appendix B, with the modification that the different dilutions were plated onto MacConkey agar.

The results of this experiment are summarized in Table 3.

TABLE 3

E. Coli experiment (CFU/ml)

| CATHETER TYPE | TIME | DAY 1 S | DAY 1 CS | DAY 2 S | DAY 2 CS | DAY 4 S | DAY 4 CS | DAY 7 S | DAY 7 CS | DAY 7+ S | DAY 7+ CS |
|---|---|---|---|---|---|---|---|---|---|---|---|
| BARDEX | A | $7 \times 10^4$ | $2 \times 10^7$ | $2 \times 10^6$ | $6 \times 10^7$ | N.D | $10^8$ | $3 \times 10^6$ | $10^9$ | $1.6 \times 10^6$ | $7 \times 10^8$ |
|  | B | $6 \times 10^4$ | $10^7$ | $2 \times 10^5$ | $10^8$ | N.D | $2 \times 10^0$ | $3 \times 10^6$ | $4 \times 10^8$ | $1.4 \times 10^6$ | $10^8$ |
|  | $\epsilon$ | $6.5 \times 10^4$ | $1.5 \times 10^7$ | $2 \times 10^5$ | $0.8 \times 10^8$ | N.D | $1.5 \times 10^8$ | $3 \times 10^6$ | $0.7 \times 10^9$ | $1.5 \times 10^6$ | $4 \times 10^8$ |
| $C_3$ | A | $<10^3$ | $<10^3$ | $<10^3$ | $<10^3$ | N.D | $<10^3$ | $<10^3$ | $<10^3$ | $<10^3$ | $<10^3$ |
|  | B | $<10^3$ | $<10^3$ | $<10^3$ | $<10^3$ | N.D | $<10^3$ | $<10^3$ | $<10^3$ | $<10^3$ | $<10^3$ |
|  | $\epsilon$ | $<10^3$ | $<10^3$ | $<10^3$ | $<10^3$ | N.D | $<10^3$ | $<10^3$ | $<10^3$ | $<10^3$ | $<10^3$ |
| D (uncoated control) | A | $10^5$ | $3 \times 10^8$ | $2 \times 10^5$ | $4 \times 10^8$ | N.D | $3 \times 10^8$ | $10^6$ | $3 \times 10^8$ | $10^6$ | $8 \times 10^8$ |
|  | B | $10^5$ | $4 \times 10^8$ | $8 \times 10^4$ | $7 \times 10^7$ | N.D | $4 \times 10^8$ | $4 \times 10^6$ | $10^8$ | $1.5 \times 10^6$ | $9 \times 10^8$ |
|  | $\epsilon$ | $10^5$ | $3.5 \times 10^8$ | $1.4 \times 10^5$ | $2.35 \times 10^8$ | N.D | $3.6 \times 10^8$ | $0.7 \times 10^6$ | $2 \times 10^8$ | $1.25 \times 10^6$ | $8.5 \times 10^8$ |

Note:
($\epsilon$) = average of the duplicate samples.
(N.D) = Not determined

EXAMPLE 5

Four tubes, about 2 inches long, made of untreated silicone (control), another four of an experimental catheter product, another four of "Bardex" (a silver-hydrogel coated catheter made by Bard Urological Products, Atlanta, USA), and another four catheters coated as described in Example 1 were used in this experiment. The tubes Were flash sterilized in 70 wt % ethanol and were let air dry in a sterile environment. Each sample of the catheter pieces was added to a sterile tube. To each tube was add 0.9 mL synthetic urine and 0.1 mL of innoculum containing ~$10^6$ cfu/mL of the organism being tested. The tubes were incubated overnight at 37° C., then decanted and the solutions were replaced for Days 2 to 4. The following tests were performed on the Day 1 samples.

For each sample to be tested, 4 sterile tubes were filled with PBS, the first three not accurately measured, and the fourth one accurately measured to 5 mL. The sample was vortexed in the innoculum solution for 5 seconds. Each sample was transferred to a PBS containing tube. The plate contacting the innoculum was swabed. The sample was vortexed with PBS containing the samples for 20 seconds and was transfer to another sterile tube containing PBS. The process was repeated 2 more times. After the last vortexing, the samples were removed with sterile forceps and the cell was scraped with a cell scraper all around the tube for about ~8 scrapes. The sample and the cell scraper tip were added to the sterile tube containing 5 mL PBS. The contents were vortexed for a short time and kept in an ultrasonic bath for 10 minutes to release the biofilm into solution. Then 0.1 mL of each of the resulting solutions was plated onto agar plates, followed by incubation at 37 C. The following graph gives the results:

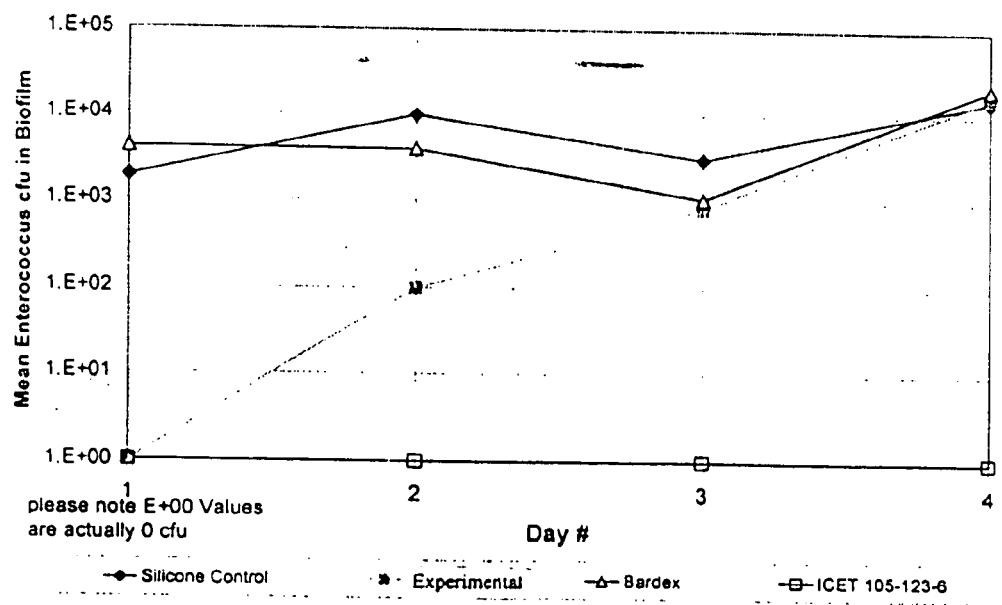

I claim:

1. An article having an antimicrobial coating made by
   (A) applying to an uncoated article an antimicrobial composition that comprises
      (1) about 5 to about 25 wt % of an antimicrobial formulation that comprises
         (a) about 40 to about 65 wt % of an antimicrobial material;
         (b) about 1 to about 55 wt % calcium chelator;
         (c) about 0.00 1 to about 0.25 wt % pigment; and
         (d) about 0.5 to about 5 wt % polyethylene oxide; and
      (2) about 75 to about 95 wt % of a silicone resin; and
      (3) an optional non-toxic organic solvent; and
   (B) permitting said coating to form on said uncoated article, whereby said antimicrobial material leaches from said antimicrobial formulation, keeping the surface of said coating free of live bacteria, yeasts, and molds.

2. An article according to claim 1 wherein said antimicrobial material is selected from the group consisting of silver, silver-copper, partially water soluble compounds of silver, silver pyrithione, zinc pyrithione, bismuth pyrithione, parabenzoic acid esters, and mixtures thereof.

3. An article according to claim 1 wherein said antimicrobial material contains silver and copper particles that are less than about 100 nm in size.

4. An article according to claim 1 wherein said antimicrobial material includes silver, copper, and parabenzoic acid esters.

5. An article according to claim 1 wherein said antimicrobial material is silver-copper nanoparticles.

6. An article according to claim 1 wherein said calcium chelator is citric acid, ethylene diamine tetraacetic acid, or a mixture thereof.

7. An article according to claim 1 wherein said pigment is copper phthalocyanine.

8. An article according to claim 1 that includes about 0.5 to about 4 wt % titanium dioxide.

9. An article according to claim 1 wherein said silicone resin is dispersed ma solvent at about 40 to about 60 w/v %.

10. An article according to claim 9 wherein said solvent is hexane.

11. An article according to claim 1 wherein said article is a Foley catheter.

12. An article according to claim 11 wherein said Foley catheter is made of silicone.

13. An article according to claim 1 wherein said silicone resin is a liquid silicone resin.

14. An article according to claim 1 wherein said silicone resin is a solid silicone resin.

15. An article according to claim 1 wherein said silicone resin is an RTV silicone resin.

16. An article according to claim 1 wherein said antimicrobial coating is formed on the surface of said uncoated article by molding, overmolding, or extruding.

17. A Foley catheter having an antimicrobial coating made by
   (A) applying to an uncoated catheter an antimicrobial composition that comprises
      (1) about 5 to about 1 wt % of an antimicrobial formulation that comprises
         (a) about 15 to about 1 wt % of an antimicrobial material that includes silver, copper, and parabenzoic acid esters;
         (b) about 20 to about 1 wt % citric acid and about 20 to about 1 wt % ethylene diamine tetraacetic acid;
         (c) about 0.1 to about 0.1 wt % pigment;
         (d) about 4 to about 5 wt % polyethylene oxide; and
         (e) about 0 to about 4 wt % titanium dioxide; and
      (2) about 88 to about 95 wt % of a dispersion of about 40 to about 60 w/v % of an RTV silicone in a solvent selected from the group consisting of hexanes, methyl ethyl ketone, and xylenes whereby said antimicrobial material slowly leaches from said antimicrobial formulation, keeping the surface of said coating free of live bacteria, yeasts, and molds.

18. A catheter according to claim 15 wherein said antimicrobial material has a particle size of less than 100 nm.

19. A catheter according to claim 15 wherein said solvent is hexane.

20. A Foley catheter having an antimicrobial coating made by applying to an uncoated catheter an antimicrobial composition that comprises
   (1) about 5 to about 12 wt % of an antimicrobial formulation that comprises
      (a) about 15 to about 1 wt % of an antimicrobial material that includes silver, copper, and parabenzoic acid esters;
      (b) about 20 to about 1 wt % citric acid and about 20 to about 1 wt % ethylene diamine tetraacetic acid;
      (c) about 0.005 to about 0.01 wt % pigment;
      (d) about 2 to about 5 wt % polyethylene oxide; and
      (e) about 0 to about 4 wt % titanium dioxide; and
   (2) about 88 to about 95 wt % of a liquid silicone resin whereby said antimicrobial material leaches from said antimicrobial formulation, keeping the surface of said coating free of live bacteria, yeasts, and molds.

21. A catheter according to claim 20 wherein said antimicrobial material has a particle size of less than 100 nm.

22. A catheter according to claim 20 wherein said solvent is hexane.

* * * * *